United States Patent [19]

Stock

[11] Patent Number: 5,043,268

[45] Date of Patent: Aug. 27, 1991

[54] SUBSTRATES AND INHIBITORS FOR PRENYL CYSTEINE METHYLTRANSFERASE ENZYMES

[75] Inventor: Jeffry B. Stock, Princeton, N.J.

[73] Assignee: The Trustees of Princeton University, Princeton, N.J.

[21] Appl. No.: 519,151

[22] Filed: May 4, 1990

[51] Int. Cl.$^5$ .................. C12Q 1/48; C07C 319/00; C07C 321/00; C07C 323/00

[52] U.S. Cl. .................................. 435/15; 435/193; 568/39; 568/41; 568/44; 568/45; 568/59

[58] Field of Search .................. 435/15, 193; 558/230; 568/39, 41, 44, 45, 59

[56] References Cited

U.S. PATENT DOCUMENTS 4,287,300  9/1981  Gibbons et al. .................. 435/5

OTHER PUBLICATIONS

Clarke et al., Proc. Natl. Acad. Sci. U.S.A.; 85, 4643–4647, 1988.

Primary Examiner—Robert A. Wax
Assistant Examiner—Mindy B. Fleisher
Attorney, Agent, or Firm—Mathews, Woodbridge & Collins

[57] ABSTRACT

Compounds of the formula:

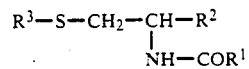

in which:
$R^1$ is alkyl of 1 to 3 carbon atoms;
$R^2$ is —COX; wherein X is hydroxy, methyl, amino, thio, H—N—(alkyl of 1 to 3 carbon atoms), N—(alkyl of 1 to 3 carbon atoms)$_2$, or halogen;
$R^3$ is a straight or branched chain alkyl of 10 to 25 carbon atoms, or a straight or branched chain alkene including polyunsaturated alkenes of 10 to 25 carbon atoms; and the alkali metal, alkaline earth metal, ammonium, and substituted ammonium salts thereof when $R^2$ is —COOH, are substrates and/or inhibitors specifically for prenyl cysteine methyltransferase enzymes which catalyze the methyl transfer from S-adenosylmethionine to the C-termini of proteins and peptides with prenylated cysteine residus at their C-termini. The compounds, as substrates, are particularly suitable for use in assays for qualitatively or quantitatively detecting the farnesyl cysteine methyltransferase enzymes.

9 Claims, No Drawings

SUBSTRATES AND INHIBITORS FOR PRENYL CYSTEINE METHYL TRANSFERASE ENZYMES

The present invention pertains to cysteine derivatives having the formula:

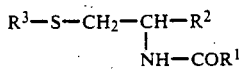

in which:

R¹ is alkyl of 1 to 3 carbon atoms;
R² is —COX; wherein X is —OH, —OCH₃, —NH₂, —NHR⁴, —N(R⁴)₂ or halogen;
R³ is a straight or branched chain alkyl of 10 to 25 carbon atoms, a straight or branched chain alkenyl, including polyunsaturated alkenes, of 10 to 25 carbon atoms;
R⁴ is an alkyl of 1 to 3 carbon atoms; and
the alkali metal, alkaline earth metal, ammonium, and substituted ammonium salts thereof when R² is —COOH.

The term alkyl as used herein for R¹ denotes a straight or branched univalent aliphatic group of 1 to 3 carbon atoms including methyl, ethyl, propyl, and the branched isomer thereof such as isopropyl.

The term "straight or branched chain alkyl" as used for R³ denotes groups including decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, and the branched isomers thereof.

The term "straight or branched chain alkenyl including polyunsaturated alkenes" as used herein for R³ denotes groups including decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, the branched chain isomers thereof, and polyunsaturated alkenes including octadec-9,12-dienyl, octadec-9,12,15-trienyl, and eicos-5,8,11,14-tetraenyl.

The compounds of Formula I have the ability to function as a substrate for a specific type of methyltransferase enzymes. These enzymes catalyze the transfer of methyl groups from S-adenosylmethionine to the C-terminal carboxylic acid groups of proteins and peptides, including GTP-binding proteins, which have the characteristic prenylated cysteine residue at their C-terminus.

The preferred compounds of Formula I are those wherein R¹ is methyl. Also preferred are compounds wherein R¹ is methyl, R² is a carboxyl group, and R³ has 14 to 20 carbon atoms. A third group of preferred compounds are those of Formula I wherein R¹ is methyl, R² is a carboxyl group, and R³ is a polyisoprenoid of 15 to 20 carbon atoms and having the isoprene structure

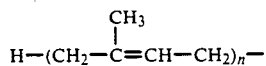

in which n is 3 or 4.

A particularly preferred compound of Formula I is that wherein R¹ is methyl, R² is a carboxyl group, and R³ is t,t-farnesyl.

Enzymes which catalyze the transfer of methyl groups from S-adenosylmethionine to the protein carboxylic acid groups, and which are termed generally as protein carboxyl methyltransferases, are known.

The first group of protein carboxyl methyltransferase (protein-glutamate methyltransferase, S-adenosyl-L-methionine: protein-L-glutamate O-methyltransferase, EC 2.1.1.24), is found in chemotactic bacteria and regulates the output of bacterial chemoreceptor proteins. It specifically and stoichiometrically methylates several glutamic acid residues on membrane-bound receptor proteins. (Clarke, et al:, Proc. Natl. Acad. Sci. USA, 85 4643–4647, 1988).

A second group of protein carboxyl methyltransferase enzymes, (protein-D-aspartate methyltransferase, S-adenosyl-L-methionine: protein-D-aspartate O-methyltransferase, EC 2.1.1.77) plays a role in the metabolism of damaged proteins. Apparently, this second class of enzymes is specific for aspartic acid residues that have been covalently altered by isomerization and racemization reactions, the products of which are D-aspartate β-methylesters and L-isoaspartate α-methylesters.

A third group of protein carboxyl methyltransferases (prenyl cysteine methyltransferase) was noted by Clarke et al., supra. The characteristics of enzymes belonging to this class have not been fully elucidated but it appears they are widely distributed in mammalian tissues with particularly high levels in brain and testes. Paik and Kim (*Protein Methylation*, John Wiley and Sons, New York, 1986) have reported that the functions of protein carboxyl methylation in processes such as leukocyte chemotaxis and hormone secretion may reflect a general role for methylation in the regulation of small molecular weight GTP binding proteins.

Methylation of the prenylated proteins occurs through a complex enzymatic process. It appears that post-translational proteolytic cleavage removes the three amino acid residues on the carboxyl-terminal side of the prenylated cysteine, followed by carboxyl methylation of this residue. While the order of the carboxyl methylation and proteolysis has not yet been determined, carboxyl methylation appears to be the final step in the modification process. It has been determined that prenylation can occur through the addition of an polyisoprenyl, such as a farnesyl moiety, through a thioether linkage: The prenyl cysteine methyltransferase enzymes most probably recognize C-terminal prenyl cysteine groups.

Inhibitors of protein carboxyl methyltransferase such as AdoMet (³H-methyl) antagonists are also known. These, however, are nonspecific inhibitors of virtually all methylation processes. These have been reported as having anti-tumor and anti-inflammatory properties, but, the actual sites of action are not defined. In addition, these compounds do not specifically inhibit the prenyl cysteine methyltransferase enzymes.

In order to characterize the prenyl cysteine methyltransferase responsible for catalyzing the methyl transfer from S-adenosylmethionine to the C-termini of GTP binding and other proteins, a reliable and simple diagnostic tool is needed.

The compounds of this invention have high specificity for the prenyl cysteine methyltransferase enzymes. The compounds of Formula I thus are competitive substrates for (and thus can be used as competitive inhibitors of) prenyl cysteine methyltransferase enzymes which catalyze methylation of prenylated proteins and peptides. The compounds of Formula I inhibit these enzymes by functioning as the preferred substrate over the natural substrate.

The compounds of the invention are particularly suitable for use as assay reagents for qualitatively and quantitatively characterizing these enzymes.

The term "competitive substrate", as used herein, is meant to include a substance which can serve as a substrate for the enzyme whether or not a natural substrate(s) is present.

The term "inhibitor" as used herein is meant to include a substance which can inhibit the activity of the prenyl cysteine methyltransferase enzyme.

The invention also pertains to diagnostic methods for qualitatively and quantitatively detecting prenyl cysteine methyltransferase enzymes.

In addition, the enzymes related to prenyl cysteine methyltransferases appear to be involved in inflammmatory responses, and the compounds of this invention can be used in pharmaceutically acceptable compositions as anti-inflammatory agents to specifically bind to and inhibit the activity of the prenyl cysteine methyltransferase related enzymes. The compounds of the invention accordingly are useful in the treatment of arthritis and related medical conditions.

It is also contemplated that the compounds of the invention can be used in vivo as reversible specific inhibitors of the prenyl cysteine methyltransferase enzymes involved in the carboxylmethylation of proteins possessing prenylated C-termini. Specific inhibition of these enzymes can prevent carboxylmethylation of the prenylated proteins and thereby detrimentally effect the activity of the prenylated proteins. A wide variety of proteins having the penultimate aliphatic residues which are subject to prenylation and carboxyl methylation by the prenyl cysteine methyltransferase enzymes are known; a number of these is shown in Table I.

TABLE I

| Protein | Carboxyl-terminal sequence |
|---|---|
| Fungal Mating Pheromones | |
| S. cerevisiae a-factor | -Asp-Pro-Ala-Cys-Val-Ile-Ala |
| Tremella brasiliensis (A-9291-I) | -Ser-Gly-Gly-Cys |
| Tremella mesenterica (A-10) | -Asn-Gly-Tyr-Cys |
| R. toruloides Rhodotorucine A | -Arg-Asn-Gly-Cys-Thr-Val-Ala |
| Ras Proteins | |
| Human/mouse Ha-ras | -Ser-Cys-Lys-Cys-Val-Leu-Ser |
| Human Ha-ras-1 variant | -Ser-Ser-Lys-Cys-Val-Leu-Ser |
| Rat Ha-ras-1 | -Ser-Cys-Lys-Cys-Val-Leu-Ser |
| Chicken Ha-ras-1 | -Asn-Cys-Lys-Cys-Val-Ile-Ser |
| Human Ki-ras-2A | -Ile-Lys-Lys-Cys-Ile-Ile-Met |
| Mouse Ki-ras-2A | -Ile-Lys-Lys-Cys-Val-Ile-Met |
| Human Ki-ras-2B | -Lys-Thr-Lys-Cys-Val-Ile-Met |
| Rat Ki-ras-2B | -Arg-Thr-Arg-Cys-Ile-Val-Met |
| Mouse Ki-ras-2B | -Arg-Thr-Arg-Cys-Thr-Val-Met |
| Human N-ras | -Gly-Leu-Pro-Cys-Val-Val-Met |
| Mouse N-ras | -Gly-Ser-Pro-Cys-Val-Leu-Met |
| Drosophila Dras1 | -Arg-Phe-Lys-Cys-Lys-Met-Leu |
| Drosophila Dras2/64B | -Lys-Arg-Lys-Cys-Cys-Leu-Met |
| Dictyostellium Ddras | -Lys-Lys-Gln-Cys-Leu-Ile-Leu |
| S. pombe SPRAS | -Thr-Lys-Cys-Cys-Val-Ile-Cys |
| S. cerevisiae RAS1 | -Gly-Gly-Cys-Cys-Ile-Ile-Cys |
| S. cerevisiae RAS2 | -Gly-Gly-Cys-Cys-Ile-Ile-Ser |
| Ras-Related Small G-Proteins | |
| Drosophila Dras3 | -Lys-Val-Pro-Cys-Val-Leu-Leu |
| Human/mouse R-ras | -Gly-Cys-Pro-Cys-Val-Leu-Leu |
| Human rapla/Krev-1 | -Lys-Lys-Ser-Cys-Leu-Leu-Leu |
| Human rap1B | -Lys-Ser-Ser-Cys-Gln-Leu-Leu |
| Human rap2 | -Lys-Ser-Pro-Cys-Val-Leu-Met |
| Aplysia rho | -Lys-Gly-Gly-Cys-Val-Val-Leu |
| Human rhoA | -Lys-Ser-Gly-Cys-Leu-Val-Leu |
| Human rhoB | -Ile-Asn-Cys-Cys-Lys-Val-Leu |

TABLE I-continued

| Protein | Carboxyl-terminal sequence |
|---|---|
| Human rhoC | -Arg-Arg-Gly-Cys-Pro-Ile-Leu |
| Human rac1 | -Lys-Arg-Lys-Cys-Leu-Leu-Leu |
| Human rac2 | -Lys-Arg-Ala-Cys-Ser-Leu-Leu |
| Human ralA | -Arg-Glu-Arg-Cys-Cys-Ile-Leu |
| Human ralB | -Lys-Glu-Arg-Cys-Cys-Leu-Leu |
| Saguinus oedipus ral | -Arg-Glu-Arg-Cys-Cys-Ile-Leu |
| S. cerevisiae RHO1 | -Lys-Lys-Lys-Cys-Val-Leu-Leu |
| S. cerevisiae RHO2 | -Ala-Asn-Cys-Cys-Ile-Ile-Leu |
| S. cerevisiae RSR1 | -Ala-Ser-Thr-Cys-Thr-Ile-Leu |
| Heterotrimeric (large) G-Proteins | |
| Bovine brain G-protein (gamma-subunit) | -Lys-Phe-Phe-Cys-Ala-Ile-Leu |
| Bovine transducin (gamma-subunit) | -Lys-Gly-Gly-Cys-Val-Ile-Ser |
| S. cerevisiae STE18 (gamma-subunit) | -Ser-Val-Cys-Cys-Thr-Leu-Met |
| Nuclear Lamin Proteins | |
| Human Lamin A | -Pro-Gln-Asn-Cys-Ser-Ile-Met |
| Xenopus laevis Lamin A | -Pro-Gln-Asn-Cys-Ser-Ile-Met |
| Chicken Lamin A | -Pro-Gln-Gly-Cys-Ser-Ile-Met |
| Murine Lamin B | -Glu-Arg-Ser-Cys-Val-Val-Met |
| Chicken Lamin B1 | -Glu-Arg-Ser-Cys-Val-Val-Met |
| Chicken Lamin B2 | -Ser-Arg-Gly-Cys-Leu-Val-Met |
| Xenopus laevis L<sub>I</sub> | -Asn-Lys-Asn-Cys-Ala-Ile-Met |
| Xenopus laevis L-III | -Asp-Pro-Ser-Cys-Ser-Ile-Met |
| Drosophila Lamin B | -Asn-Glu-Lys-Cys-Ala-Ile-Met |
| Additional Proteins | |
| Bovine cGMP phosphodiesterase (α-subunit) | -Ser-Lys-Ser-Cys-Cys-Val-Gln |
| Human cAMP phosphodiesterase | -Leu-Gln-Ser-Cys-Thr-Ile-Ile |
| Human extracellular superoxide dismutase | -Glu-Ser-Glu-Cys-Lys-Ala-Ala |
| Human (2'-5') oligo (A) synthetase E18 | -Asp-Trp-Thr-Cys-Thr-Ile-Leu |
| Mouse (2'-5') oligo (A) synthetase | -Asp-Trp-Thr-Cys-Ile-Leu-Leu |
| Human/rat gap junction protein | -Ser-Asp-Arg-Cys-Ser-Ala-Cys |
| Leukemia antigen | -Glu-Lys-Lys-Cys-Arg-Val-Trp |
| Rabbit phosphorylase kinase (α-subunit) | -His-Ser-Ile-Cys-Ala-Met-Gln |

As can be seen from the above, the ras family of oncogenes also possess the characteristic -C-aa-aa-aa sequence which functions as a signal for prenylation, proteolytic cleavage and methylation. Since it appears the carboxyl methylation is required for the activation of the gas oncogene, it may be possible through the use of the compounds of the invention to prevent activation of the ras oncogene by inhibiting in vivo the activity of the farnesyl cysteine methyltransferase responsible for the carboxyl methylation.

The compounds of this invention can be synthesized using conventional methods of condensing L-cysteine hydrochloride with t,t-farnesylbromide, followed by acetylation of the condensation product.

The following nonlimiting examples will serve to further illustrate the invention.

EXAMPLE 1

Preparation of S-trans,trans-Farnesyl-L-Cysteine

L-Cysteine hydrochloride (4 g., 25 mmol) is dissolved in 25 mL of 2N sodium hydroxide and 30 mL of ethanol. To this mixture are added 8.4 mL (28 mmol) of t,t-farnesyl bromide, followed by stirring for 30 minutes. After precipitation of S-t,t-farnesyl-L-cysteine, the pH is adjusted to 6-7 and the mixture cooled in ice water. The precipitate is removed by filtration, washed with water, ethanol, and ether.

EXAMPLE 2

Preparation of N-Acetyl, S-trans,trans-farnesyl-L-cysteine

S-t,t-farnesyl-L-cysteine (1.15 g., 3.5 mmol), as prepared in the above example, is vigorously stirred in a solution containing 2 mL of tetrahydrofuran. To this mixture is added 0.415 mL (1.25 eq., 4.4 mmol) of acetic anhydride. The mixture then is stirred for 1.5 hours while maintaining the pH at 9–10 with 2N sodium hydroxide. The pH then is adjusted to 7 by the addition of acetic acid, and the tetrahydrofuran is removed by vacuum. The resulting aqueous solution is extracted with ether and the pH adjusted to 2 by addition of 2N hydrochloric acid. The acidic solution then is extracted three times with 4 mL of ethyl acetate. The organic extract is washed with water and dried over magnesium sulfate.

$^1$H-NMR (270 MHz, CDCl$_3$) δ 8.33–8.6 (m, 1H), δ 6.37 (d, 1H), δ 5.19 (t, 1H), δ 5.07 (t, 2H), δ 4.75 (dd, 1H), δ 3.16 (m, 2H), δ 2.98 (dd, 1H), δ 2.89 (dd, 1H), δ 1.89–2.13 (m, 8H), δ 2.01 (s, 3H), δ 1.61 (s, 3H), δ 1.59 (s, 3H), δ 1.55 (s, 3H).

EXAMPLE 3

Prenyl cysteine methyltransferase assay

To a putative source of prenyl cysteine methyl transferase enzyme is added 50 μM of N-acetyl-S-farnesyl cysteine ("AFC") and 5.0 μM ($^3$H-methyl)-S-adenosylmethionine (specific activity 16,000 cpm/pmol) in 100 mM tris-HCl, 1 mM EDTA, 1 mM DTT, pH 7.9 in a final volume of 150 μL. After heating the mixture at 37° C. for 5 to 25 minutes, 25 μL of the mixture is removed and added to 250 μL of heptane. The mixture is immediately vortexed to extract N-acetyl-S-farnesyl cysteine methyl ester into the organic phase. The mixture then is centrifuged for 30 seconds, and placed in a dry ice/acetone bath to quench the reaction. The heptane layer (200 μL) is removed and added to a 1.5 mL capless Eppendorf microcentrifuge tube. The heptane is evaporated in a Speedvac, and 25 μL of 1M sodium hydroxide is added to the remaining residue. The $^3$H-methanol produced from the hydrolysis of the $^3$H-methylesters is assayed by the vapor-phase equilibrium procedure as described in Stock, J. B., et al. (1984) Methods Enzymology, 106, 310–321 which is incorporated herein by reference.

A sample of 0.003 grams of 83,000×g. pellet from homogenized bovine brain after previous removal of the 14,000×g. pellet was subjected to the foregoing assay. The results are presented in Table II.

TABLE II

| Time (min.) | cpm (w/50 μM AFC) | cpm (w/o AFC) |
|---|---|---|
| 5 | 199.5 | 41.5 |
| 10 | 343.5 | 34.5 |
| 15 | 393.5 | 56.5 |
| 20 | 543.0 | 42.0 |
| 25 | 616.0 | 31.5 |

What is claimed is:

1. A compound selected from the group of the formula:

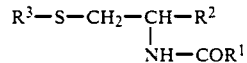

in which:
R$^1$ is alkyl of 1 to 3 carbon atoms;
R$^2$ is —COX; wherein X is —OH, —OCH$_3$, —NH$_2$, —NHR$^4$, —N(R$^4$)$_2$, or halogen;
R$^3$ is a straight or branched chain alkyl of 10 to 25 carbon atoms, or a straight or branched chain alkene of 10 to 25 carbon atoms;
R$^4$ is alkyl of 1 to 3 carbon atoms; and
the alkali metal, alkaline earth metal, ammonium, and substituted ammonium salts thereof when R$^2$ is COOH.

2. A compound according to claim 1 wherein R$^1$ is methyl.

3. A compound according to claim 1 wherein R$^2$ is —COOH.

4. A compound according to claim 1 wherein R$^3$ is farnesyl.

5. The compound according to claim 1 wherein R$^1$ is methyl, R$^2$ is —COOH, and R$^3$ is farnesyl.

6. The compound according to claim 1 where R$^1$ is methyl, X is methyl, and R$^3$ is farnesyl.

7. A method for characterizing prenyl cysteine methyltransferase enzymes comprising assaying a solution containing said enzymes with a compound according to claim 1.

8. A method of providing a competitive substrate for prenyl cysteine methyltransferase enzymes which comprises bringing a compound according to claim 1 into contact with said enzyme.

9. A method of inhibiting the activity of prenyl cysteine methyltransferase enzymes which comprises bringing a compound according to claim 1 into contact with said enzyme.

* * * * *

UNITED STATES PATENT AND TRADEMARK OFFICE
CERTIFICATE OF CORRECTION

PATENT NO. : 5,043,268
DATED     : August 27, 1991
INVENTOR(S) : Jeffry B. Stock It is certified that error appears in the above-identified patent and that said Letters Patent is hereby corrected as shown below:

In column 1, following the title and before the first line (line 5), insert the following paragraph:

"This invention was made with government support under grant AI-20980 awarded by the National Institute of Health. The government has certain rights in the invention."

Signed and Sealed this

Tenth Day of August, 1993

Attest:

MICHAEL K. KIRK

Attesting Officer

Acting Commissioner of Patents and Trademarks